United States Patent [19]

Hatfield

[11] 4,091,214
[45] May 23, 1978

[54] DE-ESTERIFICATION PROCESS FOR CEPHALOSPORINS

[75] Inventor: Lowell D. Hatfield, Bargersville, Ind.

[73] Assignee: Eli Lilly and Company, Indianapolis, Ind.

[21] Appl. No.: 772,153

[22] Filed: Feb. 25, 1977

[51] Int. Cl.$^2$ .................. C07D 501/20; C07D 501/04
[52] U.S. Cl. ...................................... 544/30; 424/246; 544/21; 544/19
[58] Field of Search ...................... 260/243 C; 544/30

[56] References Cited

U.S. PATENT DOCUMENTS

| | | | |
|---|---|---|---|
| 3,632,850 | 1/1972 | Garbrecht | 260/243 C |
| 3,781,282 | 12/1973 | Garbrecht | 260/243 C |
| 3,799,924 | 3/1974 | Jackson | 260/243 C |
| 3,828,026 | 8/1974 | Woodward | 260/239.1 |

*Primary Examiner*—Nicholas S. Rizzo
*Attorney, Agent, or Firm*—William B. Scanlon; Arthur R. Whale

[57] ABSTRACT p-Nitrobenzyl esters of cephalosporins are reductively cleaved with zinc and α-hydroxycarboxylic acids, e.g., the p-nitrobenzyl ester of the cephalosporin antibiotic, cephalexin, is reacted in an inert solvent with zinc and mandelic acid to provide the antibiotic, cephalexin, as the free acid in yields greater than 85 percent.

11 Claims, No Drawings

DE-ESTERIFICATION PROCESS FOR CEPHALOSPORINS

BACKGROUND OF THE INVENTION

This invention relates to a process for the de-esterification of cephalosporin esters. In particular, it relates to a process for the de-esterification of p-nitrobenzyl esters of cephalosporins. Esters of cephalosporins are commonly employed intermediates in the synthesis of cephalosporin antibiotics in the free acid form. The ester function is generally employed to block or protect the acidic carboxylic acid function in the molecule while reactions at other sites in the molecule are carried out. For example, Garbrecht, U.S. Pat. No. 3,632,850 describes the use of the p-nitrobenzyl ester group in the synthesis of cephalexin. In the final step of the synthesis, this ester is cleaved via hydrogenolysis under acidic conditions. Garbrecht later describes in U.S. Pat. No. 3,781,282 the de-esterification of p-nitrobenzyl esters of cephalosporins with zinc and acid in an amide-type solvent, for example in dimethylformamide. Jackson, U.S. Pat. No. 3,799,924 describes the removal of the p-nitrobenzyl ester group of cephalosporins on treatment of the ester with sodium or potassium dithionite at a pH above about 7. More recently, in copending application Ser. No. 701,850, filed July 1, 1976, Hatfield describes a process for de-esterifying certain penicillin and cephalosporin esters including the p-nitrobenzyl ester group which comprises a reductive cleavage employing zinc and organothiols, e.g., benzenethiol.

Because of the importance of the p-nitrobenzyl esters of cephalosporin antibiotics in the synthesis of these antibiotics in the free acid antibiotic form, improved or alternative methods for the removal of this ester group continue to be the subject of investigation.

SUMMARY p-Nitrobenzyl esters of cephalosporin compounds are de-esterified in an inert solvent with zinc and an α-hydroxycarboxylic acid. The process comprises a reductive cleavage of the p-nitrobenzyl group wherein the α-hydroxycarboxylic acid functions as a proton donor in the reduction and in addition forms insoluble zinc chelates which are readily separated from the reduction mixture.

The process is carried out in commonly used organic solvents at a temperature between about 20° C. and about 75° C. High yields of the cephalosporin carboxylic acids are obtained, and owing to the ability of the α-hydroxycarboxylic acids to form insoluble zinc salt chelates, the product acids are readily isolated and purified.

DETAILED DESCRIPTION

The process of this invention comprises the de-esterification of a cephalosporin p-nitrobenzyl ester represented by the following general formula

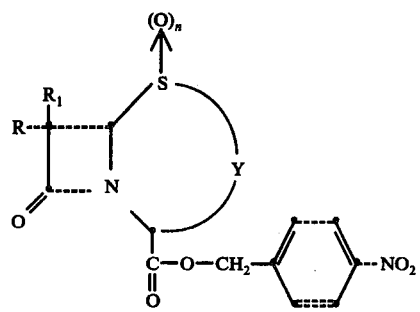

to provide the corresponding carboxylic acid represented by the formula

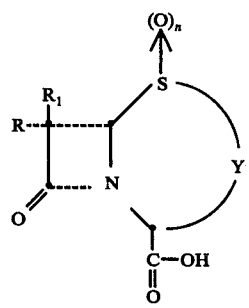

wherein $n$ is 0 or 1; R is an amino group, the ammonium group, $NH_3^{30}$, or an acylated amino group; $R_1$ is hydrogen, $C_1$–$C_4$ alkyl, $C_1$–$C_4$ alkoxy, $C_1$–$C_4$ alkylthio, carboxy or hydroxy; and Y represents one of

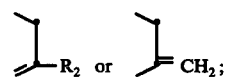

wherein $R_2$ is hydrogen or a group which is inert under the conditions of the process.

According to the process of this invention, a cephalosporin p-nitrobenzyl ester represented by the above formula I is reacted in an inert solvent at a temperature between about 20° C. and about 75° C. with zinc and an α-hydroxycarboxylic acid to provide the corresponding free acid compound represented by the above formula II. As the de-esterification proceeds, the insoluble zinc salt chelate formed with zinc and the α-hydroxycarboxylic acid forms in the reaction mixture. The insoluble salt chelate is separated from the liquid phase by filtration, decantation, or other suitable means and the de-esterification product is recovered from the liquid phase.

For best results in the process, zinc in the form of a fine dust is preferred and is employed in an amount between about 3 and about 4 moles of zinc per mole of ester; however, amounts of zinc in excess of this molar ratio can be employed. Any excess zinc remaining unreacted after the de-esterification can be separated from the reaction mixture along with the zinc salt chelate of the α-hydroxycarboxylic acid.

The α-hydroxycarboxylic acids which can be employed in the process all have the common structural feature shown below.

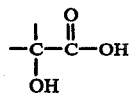

Also, dicarboxylic acids having either 1 or 2-α-hydroxy groups such as malic acid and tartaric acid can likewise be used in the de-esterification. The α-hydroxycarboxylic acids serve as proton sources in the zinc-acid reduction and in addition form highly insoluble zinc salt chelates. During the reduction, zinc metal ($Zn°$) is oxidized to divalent zinc ($Zn^{++}$). The zinc-salt complex formed with the divalent zinc and the α-hydroxycarboxylate can be depicted as shown below wherein mandelic acid is the α-hydroxycarboxylic acid.

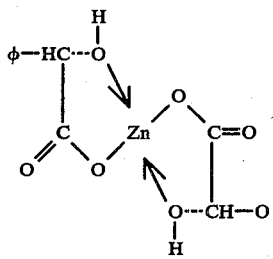

As shown above, the α-hydroxycarboxylic acids are capable of forming with the zinc cation 5-membered cyclic chelates wherein the oxygen atom of the α-hydroxy group can form a coordinate covalent bond with the zinc cation.

The α-hydroxycarboxylic acids which can be employed in the process of this invention are represented by the following structural formula

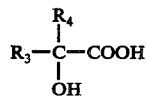

wherein $R_4$ is hydrogen, methyl, ethyl, phenyl, or phenyl substituted by halogen, lower alkyl, lower alkoxy, or hydroxy; and $R_3$ is hydrogen, methyl, ethyl, carboxymethyl, hydroxy-substituted carboxymethyl, phenyl, or phenyl-substituted by halogen, lower alkyl, lower alkoxy, or hydroxy; or $R_3$ and $R_4$ when taken together with the carbon atom to which they are attached form
 a. a 5- or 6-membered cycloaliphatic ring; or
 b. a group of the formula

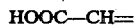

Illustrative of the α-hydroxy-substituted carboxylic acids and dicarboxylic acids represented by the above formula are glycolic acid, lactic acid, α-hydroxyisobutyric acid, mandelic acid, 4-chloromandelic acid, 3-bromomandelic acid, 4-methylmandelic acid, 4-hydroxymandelic acid, 3,4-dimethoxymandelic acid, 3,4-dichloromandelic acid, 4-ethylmandelic acid, benzilic acid, 4,4'-dichlorobenzilic acid, tartaric acid, malic acid, cis-oxalacetic (hydroxymaleic acid), and the cycloaliphatic α-hydroxy-substituted carboxylic acids, 1-hydroxycyclopentane carboxylic acid, and 1-hydroxycyclohexane carboxylic acid, and like α-hydroxy-substituted mono and dicarboxylic acids.

The α-hydroxycarboxylic acid is used in the process in a molar ratio between about 3 and about 15 moles of acid per mole of cephalosporin p-nitrobenzyl ester. Preferably, the molar ratio is about 10 to 1. Any excess α-hydroxycarboxylic acid remaining after the de-esterification is readily separated from the cephalosporin free carboxylic acid product.

Solvents which can be employed in the process are the commonly used and readily available organic solvents which are inert under the reduction conditions described herein. Such solvents include for example the amide solvents such as dimethylformamide and dimethylacetamide; nitriles such as acetonitrile, and propionitrile; ethers such as tetrahydrofuran, dioxane, and the ethers derived from glycols for example the dimethyl ether of ethylene glycol. Preferred solvents in the process of this invention are the amide solvents such as DMF and DMAC. The solvent employed in the process is preferably dry, thus enhancing the separation of the insoluble zinc salt chelate and unreacted zinc.

A preferred temperature in the process is between about 35° C. and about 65° C.

p-Nitrobenzyl esters of cephalosporin compounds wherein the cephem or cepham ring structure bears a variety of known substitution groups can be de-esterified in the process of this invention. For example, the starting materials in the process can be represented by the general structural formula I wherein R represents an amino group, the ammonium group which is representative of the amino group in salt form, or R can represent an acylated amino group or a diacylamino group. When R in the above formula represents an acylated amino group, examples of such groups include $C_2$-$C_6$ alkanoylamino, for example, acetylamino, and propionylamino; an aroylamino group such as benzoylamino or a substituted benzoylamino such as 2,6-dimethoxybenzoylamino; an aryl or heteroaryl substituted alkanoylamino group for example phenylacetylamino, 2-thienylacetylamino, 3-thienylacetylamino, 2-furylacetylamino, and tetrazoleacetylamino or such aryl or heteroaryl substituted alkanoylamino groups such as α-hydroxyphenylacetylamino, α-aminophenylacetylamino, or α-aminothienylacetylamino; or R can represent an aryloxy or arylthio substituted alkanoylamino group, for example, phenoxyacetylamino or phenylmercaptoacetylamino. In general, the acylamino group R can be any of the 7-position side chains of the known cephalosporin compounds. These acylamino side chain groups of the cephalosporins are prepared by well known acylation reactions employing an active derivative of a carboxylic acid in the acylation of a corresponding 7-aminocephalosporin nucleus compound represented by the formula I wherein R is amino. Examples of substituent groups represented by $R_1$ in the formula I are hydrogen; $C_1$-$C_4$ lower alkoxy, for example, methoxy; $C_1$-$C_4$ alkyl, for example, methyl or ethyl; carboxy; $C_1$-$C_4$ lower alkylthio, for example, methylthio or ethylthio; or $R_1$ can be hydroxy. Examples of $R_2$ substituent groups in the 3-position of the cephem nucleus include, for example, hydrogen; $C_1$-$C_4$ alkyl, for example, methyl; phenyl; halogen, for example, chloro or bromo; $C_1$-$C_4$ alkoxymethyl, for example, methoxymethyl or ethoxymethyl; $C_2$-$C_4$ alkanoyloxymethyl, for example, acetoxymethyl; and $C_1$-$C_4$ lower alkylthio methyl, for example, methylthiomethyl.

Cephalosporin p-nitrobenzyl esters as the sulfoxides (formula I, $n = 1$) can also be de-esterified in the process of this invention without concomitant reduction of the sulfoxide to the normal sulfide form.

While as stated above the de-esterification process of this invention is broadly applicable to cephalosporin p-nitrobenzyl esters, certain cephalosphorin esters are preferred. Preferred starting materials are represented by the following structural formula.

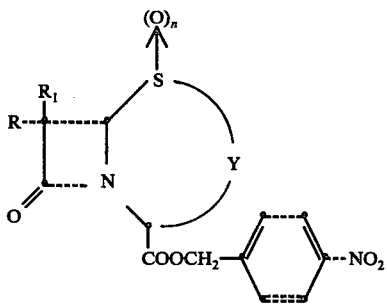

wherein Y is the group (a) or (b) of the formula

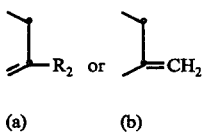

(a)      (b)

R is $H_2N-$, $H_3N^+$, phthalimido, succinimido; an acylamino group of the formula

wherein R' is hydrogen, $C_1$-$C_4$ alkyl, or cyanoacetyl; an acylamino group of the formula

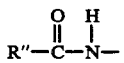

wherein R'' is phenyl or phenyl substituted by $C_1$-$C_4$ alkyl, $C_1$-$C_4$ alkoxy, halogen, hydroxy, amino, or aminomethyl; an acylamino group of the formula

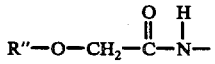

wherein R'' has the same meanings as defined above; an acylamino group of the formula

wherein R''' is R'' as defined above and in addition is 2-thienyl, 3-thienyl, 2-furyl, or 1-tetrazyl; or an α-substituted acylamino group of the formula

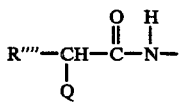

wherein R'''' is R'' and in addition is 2-thienyl, 3-thienyl, or 2-furyl, Q is —OH, —$NH_2$, —$NH_3^+$, —COOH, or —$SO_3H$; $R_1$ is hydrogen, $C_1$-$C_4$ alkyl, $C_1$-$C_4$ alkoxy, $C_1$-$C_4$ alkylthio, carboxy, or hydroxy; $R_2$ is hydrogen, $C_1$-$C_4$ alkyl, $C_1$-$C_4$ alkoxy, halogen, phenyl, $C_1$-$C_4$ alkoxymethyl, $C_1$-$C_4$ alkylthiomethyl, or a heterocyclic-thiomethyl group of the formula

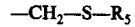

wherein $R_5$ is

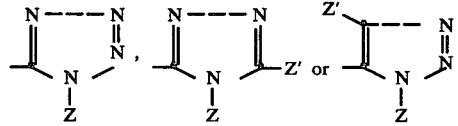

wherein Z and Z' are independently hydrogen, phenyl, or $C_1$-$C_4$ alkyl, and wherein n is 0 or 1.

When in the above definition of the preferred starting materials, R is amino, the 7-amino-3-cephem esters and the 7-amino-3-exomethylenecepham esters are described. Examples of such 7-aminocephalosporins are the p-nitrobenzyl esters of 7-amino-3-methyl-3-cephem-4-carboxylic acid, 7-amino-3-acetoxymethyl-3-cephem-4-carboxylic acid, 7-amino-7-methoxy-3-acetoxymethyl-3-cephem-4-carboxylic acid, 7-amino-7-methyl-3-acetoxymethyl-3-cephem-4-carboxylic acid, 7-amino-7-methylthio-3-acetoxymethyl-3-cephem-4-carboxylic acid, 7-amino-3-exomethylenecepham-4-carboxylic acid, 7-amino-3-methoxymethyl-3-cephem-4-carboxylic acid, 7-amino-3-methoxy-3-cephem-4-carboxylic acid, 7-amino-3-chloro-3-cephem-4-carboxylic acid, 7-amino-3-bromo-3-cephem-4-carboxylic acid, 7-amino-3-(1-methyl-1H-tetrazole-5-ylthiomethyl)-3-cephem-4-carboxylic acid, 7-amino-7-hydroxy-3-acetoxymethyl-3-cephem-4-carboxylic acid, and 7-amino-7-carboxy-3-acetoxy-3-cephem-4-carboxylic acid.

When R in the above formula represents the ammonium group ($H_3N^+$), the 7-amino compounds are represented in the salt form, for example, as an acid addition salt. Suitable acid addition salts of the 7-aminocephalosporin esters can be formed with a mineral acid such as hydrochloric acid or hydrobromic acid and with the sulfonic acids, for example, methanesulfonic acid, benzenesulfonic acid, 4-chlorobenzenesulfonic acid, and o- or p-toluenesulfonic acid.

Examples of cephalosporin esters represented by the formula I wherein R is an acylamino group R'-C(O)-NH— and R' is hydrogen are the p-nitrobenzyl esters (pNB) of the following acids: 7-formamido-3-methyl-3-cephem-4-carboxylic acid, 7-formamido-3-cephem-4-carboxylic acid, 7-formamido-3-methoxy-3-cephem-4-carboxylic acid, 7-formamido-7-methoxy-3-acetoxymethyl-3-cephem-4-carboxylic acid, and 7-formamido-7-carboxy-3-methoxymethyl-3-cephem-4-carboxylic acid; and when R' is $C_1$-$C_4$ alkyl, examples are 7-acetamido-3-acetoxymethyl-3-cephem-4-carboxylic acid, 7-acetamido-3-methyl-3-cephem-4-carboxylic acid, 7-acetamido-3-chloro-3-cephem-4-carboxylic acid, 7-acetamido-7-methoxy-3-acetoxymethyl-3-cephem-4-carboxylic acid, 7-propionamido-3-methyl-3-cephem-4-carboxylic acid, 7-butyramido-7-methylthio-3-methoxy-3-cephem-4-carboxylic acid, and 7-propionamido-3-methoxy-3-cephem-4-carboxylic acid; and when R' is cyanoacetyl, examples are 7-cyanoacetamido-3-chloro-3-cephem-4-carboxylic acid, 7-cyanoacetamido-3-acetoxymethyl-3-cephem-4-carboxylic acid, and 7-cyanoacetamido-7-methoxy-3-acetoxymethyl-3-cephem-4-carboxylic acid.

Examples of cephalosporin esters represented by the above formula when R is the acylamino group

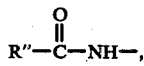

are p-nitrobenzyl 7-benzoylamino-3-methyl-3-cephem-4-carboxylate, p-nitrobenzyl 7-(2,6-dimethoxybenzoylamino)-3-methoxy-3-cephem-4-carboxylate, p-nitrobenzyl 7-(4-chlorobenzoylamino)-3-methoxymethyl-3-cephem-4-carboxylate, p-nitrobenzyl 7-benzoylamino-3-cephem-4-carboxylate, p-nitrobenzyl 7-(2-aminomethylbenzoylamino)-3-methyl-3-cephem-4-carboxylate, p-nitrobenzyl 7-(4-hydroxybenzoylamino)-3-ethoxymethyl-3-cephem-4-carboxylate and p-nitrobenzyl 7-(4-aminobenzoylamino)-3-methyl-3-cephem-4-carboxylate, and p-nitrobenzyl 7-benzoylamino-7-methoxy-3-acetoxymethyl-3-cephem-4-carboxylate.

Examples of starting materials of the above formula when R is the acylamino group

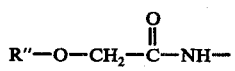

are p-nitrobenzyl 7-phenoxyacetylamino-3-methyl-3-cephem-4-carboxylate, p-nitrobenzyl 7-phenoxyacetylamino-3-methoxymethyl-3-cephem-4-carboxylate, p-nitrobenzyl 7-phenoxyacetamido-3-chloro-3-cephem-4-carboxylate, p-nitrobenzyl 7-(4-chlorophenoxyacetylamino)-3-methyl-3-cephem-4-carboxylate, p-nitrobenzyl 7-phenoxyacetylamino-3-cephem-4-carboxylate, p-nitrobenzyl 7-phenoxyacetylamino-3-exomethylenecepham-4-carboxylate, p-nitrobenzyl 7-(4-hydroxyphenoxyacetylamino)-3-methoxy-3-cephem-4-carboxylate, p-nitrobenzyl 7-phenoxyacetamido-3-bromo-3-cephem-4-carboxylate, p-nitrobenzyl 7-phenoxyacetylamino-7-methoxy-3-methyl-3-cephem-4-carboxylate, and p-nitrobenzyl 7-(3,4-dimethylphenoxyacetylamino)-3-(1-methyl-1H-tetrazole-5-ylthiomethyl)-3-cephem-4-carboxylate.

Examples of esters of the above formula when R is the acyl group

are p-nitrobenzyl 7-phenylacetylamino-3-methyl-3-cephem-4-carboxylate, p-nitrobenzyl 7-phenylacetylamino-3-methoxymethyl-3-cephem-4-carboxylate, p-nitrobenzyl 7-phenylacetylamino-7-methylthio-3-methyl-3-cephem-4-carboxylate, p-nitrobenzyl 7-phenylacetylamino-3-methoxy-3-cephem-4-carboxylate, p-nitrobenzyl 7-phenylacetamido-3-chloro-3-cephem-4-carboxylate, p-nitrobenzyl 7-[2-(2-thienyl)acetylamino]-3-methyl-3-cephem-4-carboxylate, p-nitrobenzyl 7-[2-(2-thienylacetylamino]-3-methoxymethyl-3-cephem-4-carboxylate, p-nitrobenzyl 7-[2-(2-thienyl)acetylamino]-3-bromo-3-cephem-4-carboxylate, p-nitrobenzyl 7-[2-(2-furyl)acetylamino]-3-cephem-4-carboxylate, p-nitrobenzyl 7-[(1H-tetrazole-1-yl)acetylamino]-3-methyl-3-cephem-4-carboxylate, and p-nitrobenzyl 7-(3,4-dichlorophenylacetylamino)-3-isopropoxymethyl-3-cephem-4-carboxylate.

Starting materials where in the above formula R is an α-substituted acylamino group

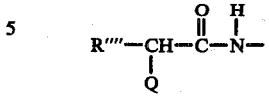

are illustrated by the following examples. p-Nitrobenzyl 7-(D-α-amino-2-phenylacetylamino)-3-methyl-3-cephem-4-carboxylate, p-nitrobenzyl 7-(D-α-amino-α-4-hydroxyphenylacetylamino)-3-methyl-3-cephem-4-carboxylate, p-nitrobenzyl 7-(D-α-amino-α-phenylacetylamino)-3-methoxymethyl-3-cephem-4-carboxylate, p-nitrobenzyl 7-(D-α-amino-α-phenylacetylamino)-3-cephem-4-carboxylate, p-nitrobenzyl 7-(D-α-amino-α-phenylacetylamino)-3-chloro-3-cephem-4-carboxylate, p-nitrobenzyl 7-(D-α-amino-α-phenylacetylamino)-3-(1,2,3-triazole-5-ylthiomethyl)-3-cephem-4-carboxylate, p-nitrobenzyl 7-(D-α-amino-α-4-hydroxyphenylacetylamino)-3-(1,2,3-triazole-5-ylthiomethyl)-3-cephem-4-carboxylate, p-nitrobenzyl 7-(D-α-amino-α-phenylacetylamino)-3-methoxy-3-cephem-4-carboxylate, p-nitrobenzyl 7-[D-α-amino-α-(2-thienyl)acetylamino]-3-methyl-3-cephem-4-carboxylate, p-nitrobenzyl 7-[D-α-amino-α-(3-thienyl)acetylamino]-3-ethoxymethyl-3-cephem-4-carboxylate, p-nitrobenzyl 7-[α-amino-α-(3-chloro-4-hydroxyphenyl)acetylamino]-3-methoxy-3-cephem-4-carboxylate, p-nitrobenzyl 7-(α-sulfo-α-phenylacetylamino)-3-methyl-3-cephem-4-carboxylate, p-nitrobenzyl 7-(α-carboxy-α-phenylacetylamino)-3-(1-methyl-1H-tetrazole-5-ylthiomethyl)-3-cephem-4-carboxylate, and p-nitrobenzyl 7-[α-amino-α-(2-furyl)acetylamino]-3-methoxymethyl-β-cephem-4-carboxylate.

An especially preferred group of esters useful in the process are represented by the following formula

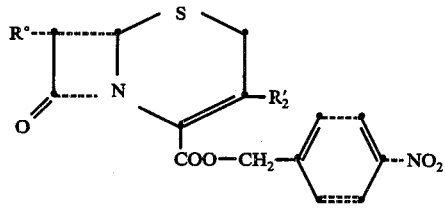

wherein $R° = H_2N-$, $H_3N^+-$, 2-thienylacetylamino, phenylacetylamino, phenoxyacetylamino, and phenylglycylamino and $R_2'$ is methyl, acetoxymethyl, methoxymethyl, chloro, bromo or methoxy.

The cephalosporin acids obtained as products of the de-esterification process of this invention are all known cephalosporin antibiotics. The cephalosporins unsubstituted in the 3-position; the 3-H-cephem compounds, are described by British Pat. No. 1,377,762. 3-Methyl-3-cephem antibiotics, the desacetoxycephalosporins, are described by Morin and Jackson U.S. Pat. No. 3,275,626 wherein 3-exomethylenecephams are also disclosed. Desacetoxycephalosporins are also described by U.S. Pat. No. 3,507,861. 3-Phenyl and 3-alkyl substituted 3-cephem compounds are described by British Pat. No. 1,405,757. The 3-methoxy-3-cephem antibiotics are described by R. R. Chauvette in U.S. Pat. Nos., 3,917,587 and 3,917,588. The 3-halo-3-cephem compounds are described by Chauvette in U.S. Pat. Nos. 3,925,372 and 3,962,227. 3-Alkoxymethyl-3-cephem antibiotics are described by Kennedy et al., U.S. Pat. Nos. 3,790,567 and 3,665,003. 3-Heterocyclicthiomethyl-substituted-3-cephem antibiotics are described for example by Ryan, U.S. Pat. No. 3,641,021, Takano et al., U.S. Pat. No. 3,516,997, Crast, U.S. Pat. No. 3,759,904 and Lemieux et al., U.S. Pat. No. 3,766,175.

As noted previously, the cephalosporin esters which can be de-esterified in the process of this invention can be substituted in the 3-position of the cephem ring with any group inert to the reaction conditions described above. The above described 3- and 7-position substituents are exemplary of such groups.

An especially preferred embodiment of this invention comprises the de-esterification of the p-nitrobenzyl ester group of the antibiotic cephalexin. In this embodiment the p-nitrobenzyl ester of cephalexin in the form of the p-toluenesulfonic acid salt is dissolved in DMF and a 10 molar excess of mandelic acid is added to the solution. The solution is agitated at room temperature and excess zinc dust is then added. The mixture is heated at about 50° C. for about 45 minutes to about 1 hour and the insoluble zinc salt chelate formed with mandelic acid is filtered. The filtrate is diluted with water and the pH adjusted to about 6.0. Cephalexin crystallizes from the diluted filtrate as the bis-DMF solvate of the zwitterionic form. This crystalline form of cephalexin is described by Garbrecht in U.S. Pat. No. 3,781,282.

In another preferred embodiment of this invention p-nitrobenzyl 7-amino-3-methyl-3-cephem-4-carboxylate hydrochloride (the pNB ester of 7-ADCA) is dissolved in DMF and tartaric acid and zinc are added to the solution. The reaction is stirred for about 1 hour at a temperature of about 55° C. and is filtered hot to remove the zinc salt chelate formed with tartaric acid. The filtrate is diluted with water and acidified to pH 1.8 with hydrochloric acid. The pH is readjusted to 4.0 with triethylamine and on standing the product, 7-ADCA, slowly crystallizes.

In yet another embodiment of the invention, p-nitrobenzyl 7-amino-3-acetoxymethyl-3-cephem-4-carboxylate (pNB ester of 7-ACA) is dissolved in dimethylacetamide and a 10 molar excess of lactic acid and a 3 molar excess of zinc dust are added with stirring. The reaction mixture is heated at a temperature between about 40 and about 50° C. for 1 hour and the zinc salt chelate is filtered while the mixture is warm. The filtrate is diluted with water and the pH is adjusted to the isoelectric point to precipitate 7-aminocephalosporanic acid (7-ACA).

The α-hydroxycarboxylic acids useful in the process are further exemplified in the following Table I. The percent yields of crystalline cephalexin bis-dimethylformamide solvate obtained with the use of a variety of α-hydroxycarboxylic acids are listed.

Table I

De-esterification of Cephalexin p-Nitrobenzyl Ester p-Toluenesulfonic Acid Salt

| α-Hydroxycarboxylic Acid | Percent Yield* |
|---|---|
| D (+) tartaric acid | 91.1 |
| L (−) tartaric acid | 85.0 |
| mandelic acid | 88.2 |
| p-chloromandelic acid | 82.3 |
| lactic acid | —** |
| glycolic acid | 70.8 |
| benzilic acid | 74.6 |

*Percent yields were based on isolated crystalline cephalexin bis DMF solvate and yields were not optimized.
**Not determined.

The α-hydroxycarboxylic acids have the ability to form chelated salts with the oxidized zinc ($Zn^{++}$) thus effectively removing the zinc from the reaction solution containing the product and allowing the product to be obtained crystalline. When the de-esterification of cephalexin p-nitrobenzyl ester was carried out with hydroxycarboxylic acids wherein the hydroxy group was located in a position other than the α-position of the acid, insoluble zinc salt chelates were not formed and the product was not obtained crystalline without taking additional isolation and purification steps. Examples of such acids are the o-hydroxy substituted aromatic carboxylic acids such as salicylic acid, 1-hydroxy-2-naphthoic acid and 3-hydroxy-2-naphthoic acid, and the hydroxy substituted aliphatic carboxylic acids such as β-hydroxybutyric acid.

The preferred α-hydroxycarboxylic acids are mandelic acid, the substituted mandelic acids, for example, p-chloro- or p-bromomandelic acid, and the tartaric acids.

The following examples are provided to further describe the process of this invention.

EXAMPLE 1

De-esterification of cephalexin p-nitrobenzyl ester tosylate salt.

To a solution of 6.55 g. (10 mMole) of cephalexin p-nitrobenzyl ester tosylate salt and 15.2 g. of D(−)-mandelic acid (100 mMole) in 50 ml. of dimethylformamide were added 1.96 g. (30 mMole) of zinc dust. The mixture was heated for 45 min. at a temperature of 50°–55° C. The precipitate of zinc mandelate and unreacted zinc were filtered before cooling and washed on the filter with dimethylformamide. The filtrate was diluted with 10 ml. of water and the pH was adjusted to 6.0 causing immediate precipitation of cephalexin. The pH was raised slowly to 6.7 and stirring was continued for one hour to complete crystallization of cephalexin. The crystalline precipitate was filtered and dried to yield 4.19 g. of cephalexin bis-DMF solvate as an off-white solid (88.2 percent yield).

EXAMPLE 2

De-esterification of p-nitrobenzyl 7-amino-3-methyl-3-cephem-4-carboxylate.

One mole of p-nitrobenzyl 7-amino-3-methyl-3-cephem-4-carboxylate is dissolved in 2 liters of dimethylformamide and 10 moles of tartaric acid and 3 gram-atoms of zinc are added with stirring. The reaction mixture is heated with continuous stirring for 3 hours at a temperature of about 50° C. The reaction mixture is filtered while hot to separate the zinc salt chelate of tartaric acid and the filtrate is diluted with about 1 liter of water. The pH of the diluted filtrate is adjusted to about 4.0 to precipitate 7-amino-3-methyl-3-cephem-4-carboxylic acid.

EXAMPLE 3

De-esterification of p-nitrobenzyl 7-(D-2-amino-2-phenylacetylamino)-3-chloro-3-cephem-4-carboxylate.

By following the procedure described in Example 1, 10 mmole of the title compound is reduced in dimethylformamide with zinc dust and glycolic acid to provide 7-(D-2-amino-2-phenylacetylamino)-3-chloro-3-cephem-4-carboxylic acid.

EXAMPLE 4

De-esterification of p-nitrobenzyl 7-phenoxyacetylamino-3-methyl-3-cephem-4-carboxylate.

The title ester is reacted with zinc dust and benzilic acid in dimethylacetamide to provide after separation of the zinc-benzilic acid salt chelate 7-phenoxyacetylamino-3-methyl-3-cephem-4-carboxylic acid.

EXAMPLE 5

De-esterification of p-nitrobenzyl 7-phenoxyacetylamino-3-methyl-3-cephem-4-carboxylate sulfoxide.

The title ester sulfoxide is reacted in dimethylacetamide with excess zinc and a 10 molar excess of p-chloromandelic acid at a temperature between about 45° and 55° C. to provide, after filtration of the zinc-p-chloromandelate salt-chelate, 7-phenoxyacetylamino-3-methyl-3-cephem-4-carboxylic acid sulfoxide.

I claim:

1. The process for de-esterifying a cephalosporin p-nitrobenzyl ester of the formula

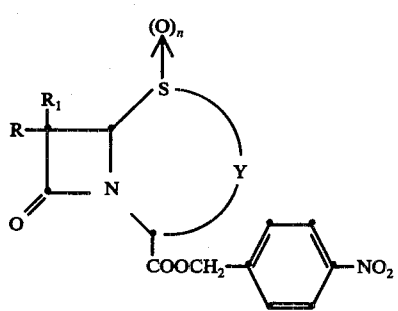

wherein Y is the group (a) or (b) of the formulas

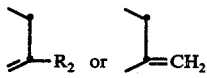

(a)  (b)

R is $H_2N-$, $H_3N^+$, phthalimido, succinimido; or an acylamino group of the formula

wherein R' is hydrogen, $C_1-C_4$ alkyl, or cyanoacetyl; an acylamino group of the formula

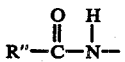

wherein R'' is phenyl or phenyl substituted by $C_1-C_4$ alkyl, $C_1-C_4$ alkoxy, halogen, hydroxy, amino, or aminomethyl; an acylamino group of the formula

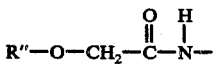

wherein R'' has the same meanings as defined above; an acylamino group of the formula

wherein R''' is R'' as defined above and in addition is 2-thienyl, 3-thienyl, 2-furyl, or 1-tetrazyl; or an α-substituted acylamino group of the formula

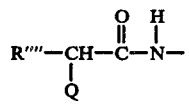

wherein R'''' is R'' and in addition is 2-thienyl, 3-thienyl, or 2-furyl, Q is $-OH$, $-NH_2$, $-NH_3^+$, $-COOH$, or $-SO_3H$; $R_1$ is hydrogen, $C_1-C_4$ alkyl, $C_1-C_4$ alkoxy, $C_1-C_4$ alkylthio, carboxy, or hydroxy; $R_2$ is hydrogen, $C_1-C_4$ alkyl, $C_1-C_4$ alkoxy, halogen, phenyl, $C_1-C_4$ alkoxymethyl, $C_1-C_4$ alkylthiomethyl, or a heterocyclicthiomethyl group of the formula

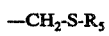

wherein $R_5$ is

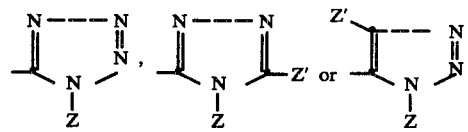

wherein Z and Z' are independently hydrogen, phenyl, or $C_1-C_4$ alkyl, and wherein n is 0 or 1, which comprises reacting said ester at a temperature between about 20° and about 75° C. in an inert solvent with between about 3 moles and about 4 moles of zinc per mole of ester in the presence of between about 3 moles and 15 moles of an α-hydroxycarboxylic acid per mole of said ester, wherein said acid is an α-hydroxycarboxylic acid of the formula

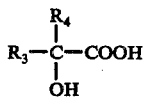

wherein $R_4$ is hydrogen, methyl, ethyl, phenyl, or phenyl substituted by halogen, lower alkyl, lower alkoxy, or hydroxy; and $R_3$ is hydrogen, methyl, ethyl, carboxymethyl, hydroxy-substituted carboxymethyl, phenyl, or phenyl-substituted by halogen, lower alkyl, lower alkoxy, or hydroxy; or $R_3$ and $R_4$ when taken together with the carbon atom to which they are attached form a. a 5- or 6-membered cycloaliphatic ring; or
b. a group of the formula

2. The process of claim 1 wherein the α-hydroxycarboxylic acid and the zinc are present in amounts corresponding to a 10 molar excess and 3 molar excess, respectively, of the cephalosporin ester.

3. The process of claim 1 wherein the de-esterification is carried out at a temperature between about 35° C. and about 65° C.

4. The process of claim 1 wherein $R_1$ is hydrogen and $n$ is 0.

5. The process of claim 4 wherein the cephalosporin p-nitrobenzyl ester is an ester of the formula

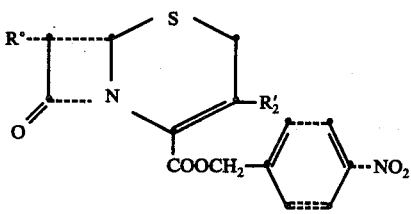

wherein R° is amino, ammonium, 2-thienylacetylamino, phenylacetylamino, phenoxyacetylamino, or phenylglycylamino, and $R_2'$ is methyl, acetoxymethyl, methoxymethyl, chloro, bromo, or methoxy.

6. The process of claim 5 wherein R° is phenylglycylamino.

7. The process of claim 6 wherein $R_2'$ is methyl, acetoxymethyl, or chloro.

8. The process of claim 7 wherein $R_2'$ is methyl.

9. The process of claim 8 wherein the α-hydroxycarboxylic acid is mandelic acid or tartaric acid.

10. The process of claim 9 which comprises the further steps of separating the insoluble zinc mandelate chelate or zinc tartarate chelate from the reaction mixture and adjusting the pH of the reaction mixture to the isoelectric point of the de-esterified cephalosporin.

11. The process of claim 10 wherein the inert solvent is dimethylformamide or dimethylacetamide.

* * * * *